(12) United States Patent
Hall et al.

(10) Patent No.: US 9,788,817 B2
(45) Date of Patent: Oct. 17, 2017

(54) URINE SPECIMEN CAPTURE SLIT

(71) Applicant: NewVistas, LLC, Provo, UT (US)

(72) Inventors: David R. Hall, Provo, UT (US); Stephen C. Davis, Salt Lake City, UT (US); Joshua D. Larsen, Spanish Fork, UT (US); Jared M. Reynolds, Pleasant Grove, UT (US)

(*) Notice: Subject to any disclaimer, the term of this patent is extended or adjusted under 35 U.S.C. 154(b) by 0 days.

(21) Appl. No.: 14/825,164

(22) Filed: Aug. 12, 2015

(65) Prior Publication Data

US 2015/0342575 A1 Dec. 3, 2015

Related U.S. Application Data

(63) Continuation-in-part of application No. 14/198,385, filed on Mar. 5, 2014, now Pat. No. 9,416,524, and a continuation-in-part of application No. 14/702,723, filed on May 2, 2015.

(60) Provisional application No. 62/036,277, filed on Aug. 12, 2014, provisional application No. 62/081,267, filed on Nov. 18, 2014, provisional application No. 62/113,934, filed on Feb. 9, 2015.

(51) Int. Cl.
*E03D 9/10* (2006.01)
*A61B 10/00* (2006.01)
*E03D 9/00* (2006.01)

(52) U.S. Cl.
CPC .............. *A61B 10/007* (2013.01); *E03D 9/00* (2013.01)

(58) Field of Classification Search
CPC ... A61B 10/007; A61B 10/0045; A61B 5/207; A61B 5/208; E03D 9/00; A61F 2013/15146; A61F 2013/8473; G01N 1/02

USPC .............. 600/573, 578, 579; 73/86.71, 864, 73/864.772, 864.83; 356/244, 73.1

See application file for complete search history.

(56) References Cited

U.S. PATENT DOCUMENTS

| | | | | |
|---|---|---|---|---|
| 3,918,433 A | * | 11/1975 | Fuisz | A61B 10/007 600/573 |
| 4,031,897 A | * | 6/1977 | Graetz | A61F 5/4401 604/347 |
| 4,961,431 A | * | 10/1990 | Ikenaga | A61B 5/20 600/573 |
| 4,962,550 A | * | 10/1990 | Ikenaga | E03D 9/00 4/314 |
| 5,111,539 A | * | 5/1992 | Hiruta | A61B 5/02241 4/301 |
| 5,184,359 A | * | 2/1993 | Tsukamura | A61B 5/02241 4/314 |
| 5,625,911 A | * | 5/1997 | Nakayama | A61B 10/007 4/661 |
| 5,720,054 A | * | 2/1998 | Nakayama | A61B 10/007 4/420 |
| 5,730,149 A | * | 3/1998 | Nakayama | A61B 10/007 600/573 |
| 5,772,606 A | * | 6/1998 | Ashibe | G01N 33/493 600/573 |
| 6,542,231 B1 | * | 4/2003 | Garrett | G01N 21/05 250/227.11 |
| 2003/0060730 A1 | * | 3/2003 | Perez | A61B 5/1411 600/576 |

(Continued)

*Primary Examiner* — J. Casimer Jacyna
*Assistant Examiner* — Benjamin R Shaw (57) ABSTRACT

The present invention relates to a urine specimen capture device comprising a narrow slit disposed on a surface exposed to urine that retains a portion of the urine specimen.

13 Claims, 8 Drawing Sheets

(56) References Cited

U.S. PATENT DOCUMENTS

| | | | |
|---|---|---|---|
| 2004/0116829 A1* | 6/2004 | Raney | A61B 5/1411 |
| | | | 600/573 |
| 2004/0179194 A1* | 9/2004 | Schmilovitch | G01N 21/05 |
| | | | 356/244 |
| 2005/0261605 A1* | 11/2005 | Shemer | A61B 10/007 |
| | | | 600/573 |
| 2006/0184064 A1* | 8/2006 | Paasch | A61B 10/007 |
| | | | 600/573 |
| 2008/0103414 A1* | 5/2008 | Song | G01N 33/558 |
| | | | 600/573 |
| 2010/0085571 A1* | 4/2010 | Robertson, Jr. | G01N 21/0303 |
| | | | 356/432 |
| 2011/0237977 A1* | 9/2011 | Knight | A61B 10/007 |
| | | | 600/573 |
| 2013/0041236 A1* | 2/2013 | Pugia | A61B 10/0045 |
| | | | 600/309 |

* cited by examiner

URINE SPECIMEN CAPTURE SLIT

FIELD OF THE INVENTION

The present invention generally relates to a device for capturing a urine specimen in a capture bowl and analyzing the urine specimen.

BACKGROUND

A urine hat is a long-standing toilet insert used to capture urine for measurement and analysis. Since it provides access to undiluted urine and does not require a change in the normal bathroom routine, it is an ideal platform for on-site urine analysis. Urine hats are widely used in hospitals and other healthcare facilities to monitor urine output.

Essentially, a urine hat is a large plastic measuring cup that sits on the rim of a toilet bowl and collects urine while the patient uses the toilet in a normal fashion. Following a urinary event, a nurse enters the patient's room, documents the level of urine in the hat, empties the contents into the toilet bowl and then flushes the toilet. Since many of the drugs or health conditions experienced during a hospital stay can affect kidney function or require good urine output, this is a simple and effective means of monitoring urine output. Additionally, urine hats are used to collect urine specimens for lab analysis both in the hospital and at home.

Unlike the typical urine sampling procedure employed by laboratories, urine hats capture a clean, complete, undiluted urine sample as part of normal toilet use. As a result, samples are easily obtained with every bathroom visit and data can be continuously acquired without interrupting the patient's normal routine.

Conventionally, however, the basic urine hat is used for little more than collecting a sample and determining the volume of urine output. Moreover, despite the convenience of a urine hat (in comparison to using a simple disposable cup), there is still some inconvenience associated with visually inspecting the contents, determining the volume of urine output, transferring the contents to a laboratory specimen container for further analysis, manually disposing of the contents, and, of course, exposing the laboratory personnel who handle the urine hat to harmful pathogens.

Accordingly, there is a need to develop a urine hat that is safer, more user friendly and more amenable to frequent use.

SUMMARY OF THE INVENTION

The present invention provides a novel urine specimen capture system for collecting, analyzing, and disposing of a urine specimen without any manual handling of the urine specimen.

In one embodiment, the present invention provides a urine specimen collection device comprising a narrow slit disposed on a surface exposed to urine, wherein at least a portion of the urine is retained within the narrow slit.

In some embodiments, the surface exposed to urine is disposed on a toilet bowl, urinal or urine hat.

In some embodiments, the surface exposed to urine comprises a raised mound and the narrow slit is disposed within the raised mound.

In yet other embodiments, the narrow slit is oriented in a direction substantially parallel to a flow of the urine. In still other embodiments, the narrow slit is oriented in a direction substantially parallel to a flow of flush water.

In yet other embodiments, the narrow slit comprises a width sufficient to retain the portion of the urine by capillary force. In other embodiments, the slit has internal sides having a hydrophilic surface.

In yet other embodiments, the slit comprises internal sides and wherein each internal side has an aperture opposing an aperture on the other internal side, through which apertures light can be transmitted and/or received by fiber optic cables optically connected with a spectrometer or other analytical device.

Thus, in some embodiments, the slit comprises internal sides and the internal sides each have opposing apertures within which an optical fiber can be inserted. Accordingly, in some embodiments, the urine capture device may further include an optical fiber that is optically connected to a spectrometer.

These and other aspects of the present invention are realized in the present specification and claims, as shown and described in the following figures and related description. It will be appreciated that various embodiments of the invention may not include each aspect set forth above and aspects discussed above shall not be read into the claims unless specifically described therein.

BRIEF DESCRIPTION OF THE DRAWINGS

The present invention is illustrated and described in reference to the accompanying drawings in which.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The skilled artisan will understand, however, that the apparatuses, systems and methods described below can be practiced without employing these specific details, or that they can be used for purposes other than those described herein. Indeed, they can be modified and can be used in conjunction with products and techniques known to those of skill in the art in light of the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

Reference in the specification to "one embodiment" or "an embodiment" means that a particular feature, structure, or characteristic described in connection with the embodiment is included in at least one embodiment, but is not a requirement that such feature, structure or characteristic be present in any particular embodiment unless expressly set forth in the claims as being present. The appearances of the phrase "in one embodiment" in various places may not necessarily limit the inclusion of a particular element of the invention to a single embodiment, rather the element may be included in other or all embodiments discussed herein.

Furthermore, the described features, structures, or characteristics of embodiments of the invention may be combined in any suitable manner in one or more embodiments. In the following description, numerous specific details are provided, such as examples of products or manufacturing techniques that may be used, to provide a thorough understanding of embodiments of the invention. One skilled in the relevant art will recognize, however, that embodiments of the invention may be practiced without one or more of the specific details, or with other methods, components, materials, and so forth. In other instances, well-known structures, materials, or operations are not shown or described in detail to avoid obscuring aspects of the invention.

Before the present invention is disclosed and described in detail, it should be understood that the present disclosure is not limited to any particular structures, process steps, or materials discussed or disclosed herein, but is extended to include equivalents thereof as would be recognized by those of ordinarily skill in the relevant art. More specifically, the invention is defined by the terms set forth in the claims. It should also be understood that terminology contained herein is used for the purpose of describing particular aspects of the invention only and is not intended to limit the invention to the aspects or embodiments shown unless expressly indicated as such. Likewise, the discussion of any particular aspect of the invention is not to be understood as a requirement that such aspect is required to be present apart from an express inclusion of the aspect in the claims.

It should also be noted that, as used in this specification and the appended claims, singular forms such as "a," "an," and "the" may include the plural unless the context clearly dictates otherwise. Thus, for example, it is understood that a reference to "an engagement element" may include one or more of such engagement elements. In particular, with respect to the construction of claims, it is further understood that a reference to "an engagement element" reads on an infringing device that has more than one engagement element, since such infringing device has "an engagement element", plus additional engagement elements. Accordingly, the use of the singular article "a," "an," and "the" is considered open-ended to include more than a single element, unless expressly limited to a single element by such language as "only," or "single."

As used herein, the term "substantially" refers to the complete or nearly complete extent or degree of an action, characteristic, property, state, structure, item, result or function as indicated. For example, an object that is "substantially" enclosed would mean that the object is either completely enclosed or nearly completely enclosed, such that it retains the function of a completely enclosed object. The exact allowable degree of deviation from absolute completeness may in some cases depend on the specific context, for example, such that enclosing an element would be substantially enclosed, even if the distal end of the structure enclosing the element had a slit or channel formed along a portion thereof. The use of "substantially" is equally applicable when used in a negative connotation to refer to the complete or near complete lack of an action, characteristic, property, state, structure, item, or result. For example, a structure which is "substantially free of" a bottom would either completely lack a bottom or so nearly completely lack a bottom that the effect would be functionally the same as if it lacked a bottom.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

The structure, function and use of the improved urine hat of the present invention is described and shown in the figures, discussed below.

In one aspect, the present invention provides a urine specimen capture device that comprises a capture bowl to capture a urine specimen, a mounting frame connected to the capture bowl to support the capture bowl within a toilet bowl and an analytic device connected to the capture bowl to analyze a property of the urine specimen in the capture bowl.

In some embodiments, the capture device may further comprise an opening at a bottom of the capture bowl to drain the urine specimen. In a particular embodiment, for example, the opening may also comprise a flow flush valve configured to selectively close and open. For example, the flush valve may close the opening during a urine specimen collection cycle so as to allow measurement and analysis of the urine specimen, and then open during a flush cycle so as to dispose of the contents of the capture bowl. The flush valve may also be configured to selectively close and open to maintain the urine specimen at a predetermined volume in the capture bowl. The predetermined volume level may be maintained by use of an analytic device that measures the volume of the urine specimen in the capture bowl. Such an analytic device may include, for example, a fluid level sensor. The fluid level sensor may be configured to detect when the urine specimen has reached a predetermined level and then provide a signal to the flush valve to release a quantity of the urine specimen so as to prevent the urine specimen from exceeding the predetermined level or fluid volume. In some embodiments, the capture device may also further comprise a flow rate sensor, which can detect the rate of flow of the urine specimen through the opening and calculate the total volume of urine specimen deposited in the capture bowl by reference to the rate of flow, over a given period of time, to calculate the volume of urine specimen that has passed through the opening. The flow rate sensor may also be used to communicate retained volume in the capture bowl, so as to assure that a sufficient amount of a urine specimen is retained in the capture bowl for purposes of analysis.

In another embodiment, the urine capture device may further include a sensor that detects the presence near or approach of a user toward the urine capture device. For example, such sensors may include such devices a pressure sensor that detects the weight of a user sitting on or standing near the urine capture device, or a proximity sensor that detects the presence of a user near the urine capture device or the approach of a user toward the urine capture device. Such sensors may include, for example, a sensor that wirelessly detects a transmitter in the possession of the user via any suitable wireless technology, such as Blue-tooth. A sensor that detects the approach of a user may be useful, for example, by enabling the urine capture device and system to begin preparations of the urine capture device for a new user, including rinsing (again) the capture bowl, closing the opening at the bottom of the capture bowl, connecting with the internet to access that user's profile and medical history records (which can be updated following receipt and analysis of that particular urine specimen), etc.

In another embodiment, the flush valve is operably connected to and configured to open upon actuation of a toilet flush mechanism. For example, during a urine specimen collection event the flush valve will be closed to enable measurement and analysis of the urine specimen. When the measurement and analysis is completed and the urine specimen is no longer needed the toilet is flushed and a signal is sent to the flush valve to open, thereby allowing the urine specimen to be released from the capture bowl. In some embodiments, described in more detail below, the flush water from the toilet may also be diverted to the capture bowl so as to rinse the capture bowl free of the urine specimen. In another embodiment, the flush valve is operably connected to a user sensor configured to close the flush valve when the presence of a user on the toilet seat is detected and open the flush valve when the presence of a user on the toilet seat is not detected. For example, the user sensor may comprise a toilet seat load (weight) sensor, or a user proximity sensor.

In another embodiment, the present invention further comprises a capture device having a mounting frame that is connected to the capture bowl and supports the capture bowl within a toilet bowl. In a particular embodiment, the mounting frame is configured to mount to a toilet bowl or toilet bowl rim. The mounting frame may mount to the toilet bowl or toilet bowl rim by means of a flange that extends from the capture bowl and is configured to lie flat on the top of the toilet bowl rim. Alternatively, the mounting frame may comprise a suction device that is configured to be firmly mounted on the toilet bowl rim or the sides of the toilet bowl rim by means of suction cups. It is further understood that the capture bowl may be mounted to the inside of the toilet bowl, without being mounted on or to the sides of the toilet bowl rim, for example by means of suction cups that are configured to adhere to the inside of the toilet bowl. Other configurations for mounting to the toilet bowl are also possible that are not disclosed herein.

In another aspect of the invention, the capture device may also comprise an analytic device connected to the capture bowl to analyze properties of the urine specimen that has been collected in the capture bowl. For example, the analytic device may comprise a spectrometer that is capable of analyzing the chemical properties of the urine sample by identifying and quantifying particular chemicals present by measuring properties of light over a specific portion of the electromagnetic spectrum.

In another embodiment, the capture device of the present invention may include a light transparent window that isolates the spectrometer from the urine specimen. The light transparent window will be transparent to those wavelengths used for spectroscopic analysis of the urine specimen. For example, the light transparent window will generally be transparent to light in the near ultraviolet to near infrared range.

In another embodiment, the analytic device, such as a spectrometer, functionally coordinates with the fluid level sensor. For example, upon the fluid level reaching a designated level, such as above the point at which the spectrometer is able to take a reading, the spectrometer may be actuated to analyze the urine specimen that has reached the designated level.

In other embodiments, the analytic device may comprise a transmitter for wireless communication of information that has been acquired by the analytic device. In some embodiments, the wireless information is communicated from the analytic device to a general purpose computer, which is configured to receive and store such information in its computer memory. For example, the data acquired by the analytic device may be stored in a computer database that includes files associated with the patient on whose behalf the data is being collected at the urine specimen collection event, and possibly at a plurality of urine specimen collection events over a period of time.

In yet another embodiment, the analytic device may further comprise a generator that powers the analytic device. For example, the generator may be operably connected to the flush water, such that the flush water upon flushing flows through a hydraulic turbine to convert the energy of flowing water into mechanical energy, which is then converted to electricity by means of a hydroelectric generator. Such electricity may be used immediately as it is generated or stored, such as in a battery, for later use.

In another aspect, the present invention provides a urine specimen capture device for analyzing a urine specimen, comprising a flush water capture flange fluidly connected to and extending from the capture bowl to capture flush water emitted from a toilet bowl rim during a toilet flush cycle and divert the flush water to the capture bowl to thereby rinse the capture bowl of the urine specimen. In one embodiment, the capture device may also include an opening at a bottom of the capture bowl to drain the urine specimen.

In some embodiments, the capture flange extends from the capture bowl a distance sufficient that an outer edge of the capture flange is, when inserted within a toilet bowl, capable of extending under one or more rim hole through which flush water is discharged from a toilet bowl rim, thereby capturing toilet flush water discharged from rim holes. In another embodiment, the capture flange extends a distance sufficient that an outer edge of the capture flange, when inserted within a toilet bowl, is capable of abutting an inside surface of the toilet bowl, thereby capturing toilet flush water discharged from rim holes and flowing down an inside surface of the toilet bowl. In order to facilitate capturing as much flush water as possible discharged through the rim holes and running down the side of the toilet bowl, the capture flange may be flexible so as to form a seal against the side of the toilet bowl, thereby increasing the amount of flush water captured.

In some embodiments, the capture flange extends from a front portion of the capture bowl, so as to catch water discharged from the front rim holes of the toilet bowl rim and divert the water to the capture bowl where it can then rinse the capture bowl substantially free of the urine specimen that has been collected and analyzed. In other embodiments, the capture flange extends from one or more side portion of the capture bowl, so as to catch water discharged from one or more side rim holes of the toilet bowl rim. In yet other embodiments, the capture flange may extend from both front and side portions of the capture bowl.

In some embodiments, the capture flange is configured to slope downwardly from the outer edge of the capture flange which extends to or near the sides of the capture bowl, such that water captured by the capture flange from one or more flush water rim hole is able to flow downwardly on the capture flange and into the capture bowl. In order to divert flush water to those areas of the capture bowl that may have been exposed to the urine specimen, some embodiments of the capture bowl may also include ridges or a plurality of ridges (or, alternatively, valleys or a plurality of valleys) that function to direct water in a desired direction, for example, toward the opening at the bottom of the capture bowl, or toward a region where the analytic device may be receiving information from the urine specimen.

In another aspect, the present invention provides a novel urine collection device that is configured to receive the urine specimen for purposes of enabling analysis by the analytic device. In one particular embodiment, for example, the novel urine collection device comprises a narrow slit disposed on a surface exposed to urine, wherein at least a portion of the urine is retained within the narrow slit. The surface may be any surface used to receive or is exposed to a urine specimen. For example, the surface may be an inside surface of a capture bowl of a urine hat (as described above), the inside surface of a toilet bowl, or the inside surface of a stand-up style urinal. In some embodiments, the surface exposed to urine may comprise a raised mound and the narrow slit is disposed within the raised mound. In other embodiments, the slit may be recessed below the surface exposed to urine, such that the urine specimen flows through the slit while retaining a sufficient quantity of the urine specimen to enable analysis of the urine specimen. In one particular embodiment, the recessed slit comprises a flow path having a downward slope throughout the flow path, such that the urine specimen and/or flush water that rinses the urine specimen out of the slit is not able to pool within the slit. In another embodiment, the recessed slit comprises a flow path having at least a portion of which is sloped upwardly so as to specifically collect or pool the urine specimen within the slit and thereby retain a portion of the urine specimen for analysis.

In yet another embodiment, the narrow slit is oriented in a direction substantially parallel to a flow of the urine. For example, in some embodiments, the slit is oriented downwardly or vertically with reference to the slope of the capture bowl or toilet bowl. In particular, the slit may be oriented such that the slit is parallel or aligned with an imaginary line that represents the maximum slope of the toilet bowl at the location of the slit (i.e., so that it is parallel with the flow of the urine specimen and flush water as it runs downwardly by gravity, straight down the toilet bowl). Alternatively, the slit may be oriented such that it directs the flow of the urine specimen and flush water at an angle relative to the direction of the flow of the urine specimen and flush water as it runs downwardly by gravity. Thus, the narrow slit may be oriented in a direction substantially parallel to the flow of flush water.

In some embodiments, the narrow slit comprises a width sufficient to retain the portion of the urine by capillary force. Capillary action may, for example, be used to wick the urine specimen within the narrow space defined by the slit and retain the urine specimen, in opposition to the external force of gravity that would ordinarily cause the urine specimen to flow downwardly out of the slit. Capillary force occurs because of intermolecular forces between the urine specimen and surround solid surfaces defined by the inside walls of the slit. If the slit is sufficiently narrow, the combination of surface tension, caused by cohesion within the liquid, and the adhesive forces between the urine specimen and the inside walls of the slit act to retain the urine specimen within the slit. In some embodiments, the slit may have internal sides having a hydrophilic surface that assist with retention of the urine specimen by hydrophilic or capillary forces.

In some embodiments, the inside surface of the urine capture bowl is coated with a hydrophobic coating or is manufactured of a hydrophobic material. The use of a hydrophobic material reduces urine specimen residue on the urine capture bowl, and promotes cleaning of urine specimen residue from the urine capture bowl during flushing.

In other embodiments, the narrow slit may have a width that is greater than that required to capture and retain a urine specimen by capillary or hydrophilic forces. For example, the width of the narrow slit may be sufficiently wide that the urine specimen flows through the slit, such that a spectrometer takes a reading and analyzes the urine specimen while the urine specimen is flowing through the slit.

In another aspect, the present invention further provides a urine specimen collection where the slit comprises internal sides and wherein each internal side has an aperture opposing an aperture on the other internal side. Each aperture may be used, for example, as a conduit for an optical fiber that transmits and/or receives light for purposes of analyzing the urine specimen by spectroscopy, where the optical fiber is optically connected to a spectrometer located remotely from the urine specimen collection device. In some embodiments the aperture includes a light transparent window through which light is transmitted or received. In other embodiments, the optical fiber is inserted and sealed within the aperture and the end of the optical fiber is exposed directly to the urine specimen, with no light transparent window between the optical fiber and the urine specimen.

The above-referenced embodiments of the present invention are further shown and described in the figures, which show particular embodiments of the invention. It is understood that the embodiments illustrated in the figures are not limiting of the invention described and claimed herein, that other embodiments of the invention are contemplated, and that the scope of the present invention should be construed solely by the disclosure and claims set forth herein.

Figure 1:
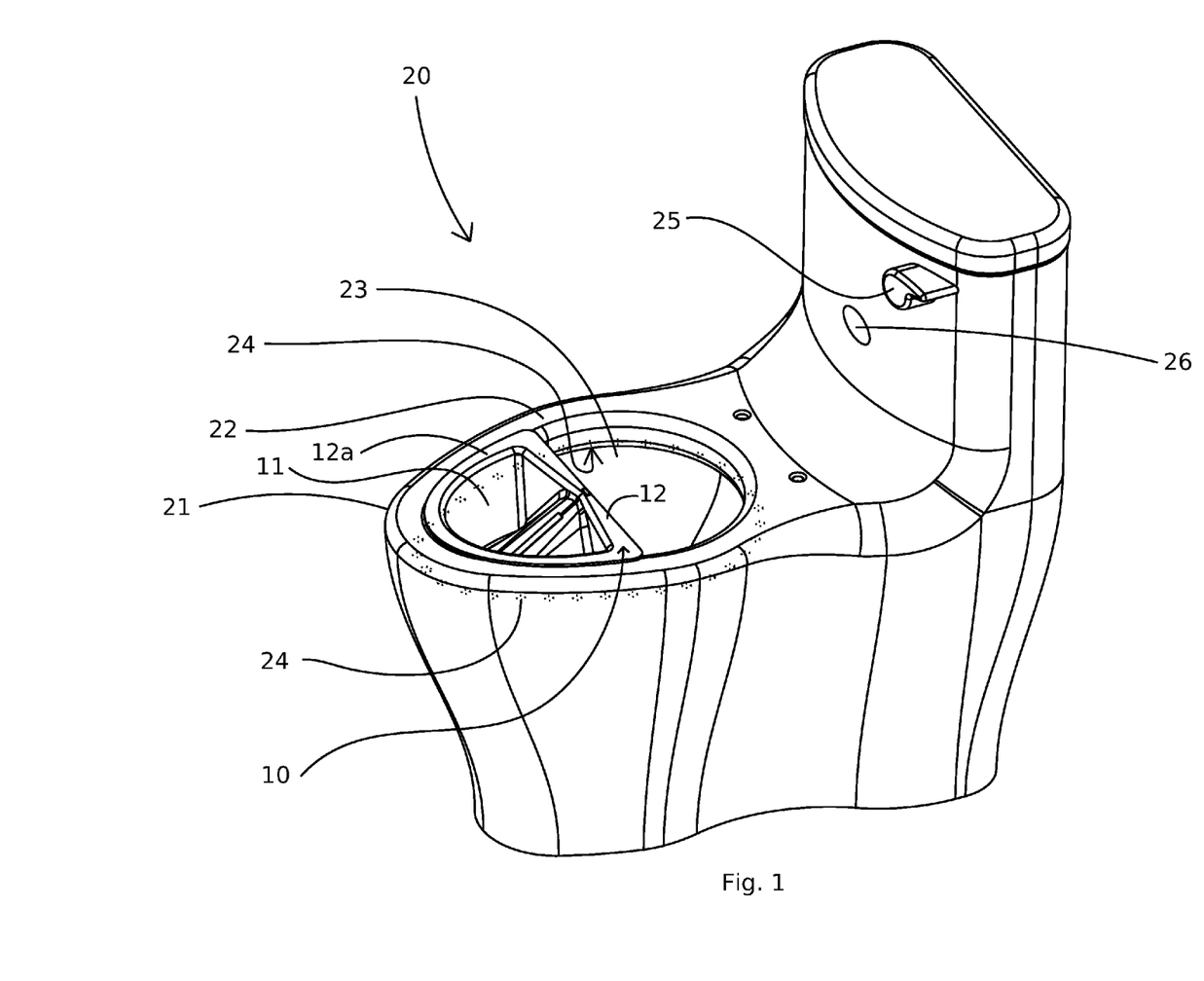
FIG. 1 is a perspective view of a toilet having placed within it a capture bowl in accordance with one embodiment of the invention.

FIG. 1 shows a perspective view of one particular embodiment of the urine capture device 20 of the present invention (shown without a toilet lid or toilet seat for ease of viewing). In FIG. 1, a urine capture bowl 10 that is capable of functioning as a urine specimen capture device is shown disposed in a toilet bowl 23. The urine capture bowl 10 is supported by a mounting frame 12, which is configured as a rim mounting flange that is mounted on the rim 22 of the toilet bowl 23. The user urinates into the capture bowl 10, and the urine specimen is retained in the urine capture bowl so that it is not diluted or contaminated by the contents of the toilet bowl. After analysis of the urine specimen is completed, the user flushes the toilet with flush handle 25 (or the toilet automatically flushes upon detecting by means of a proximity sensor 26 that the user leaves the premises), flush water from the rim holes 24 is discharged into both the toilet bowl 23, as well as the urine capture bowl 10, thereby rinsing the urine specimen from the urine capture bowl. The features of the urine capture bowl are described in greater detail in the following FIGS. 2-7.

Figure 2:
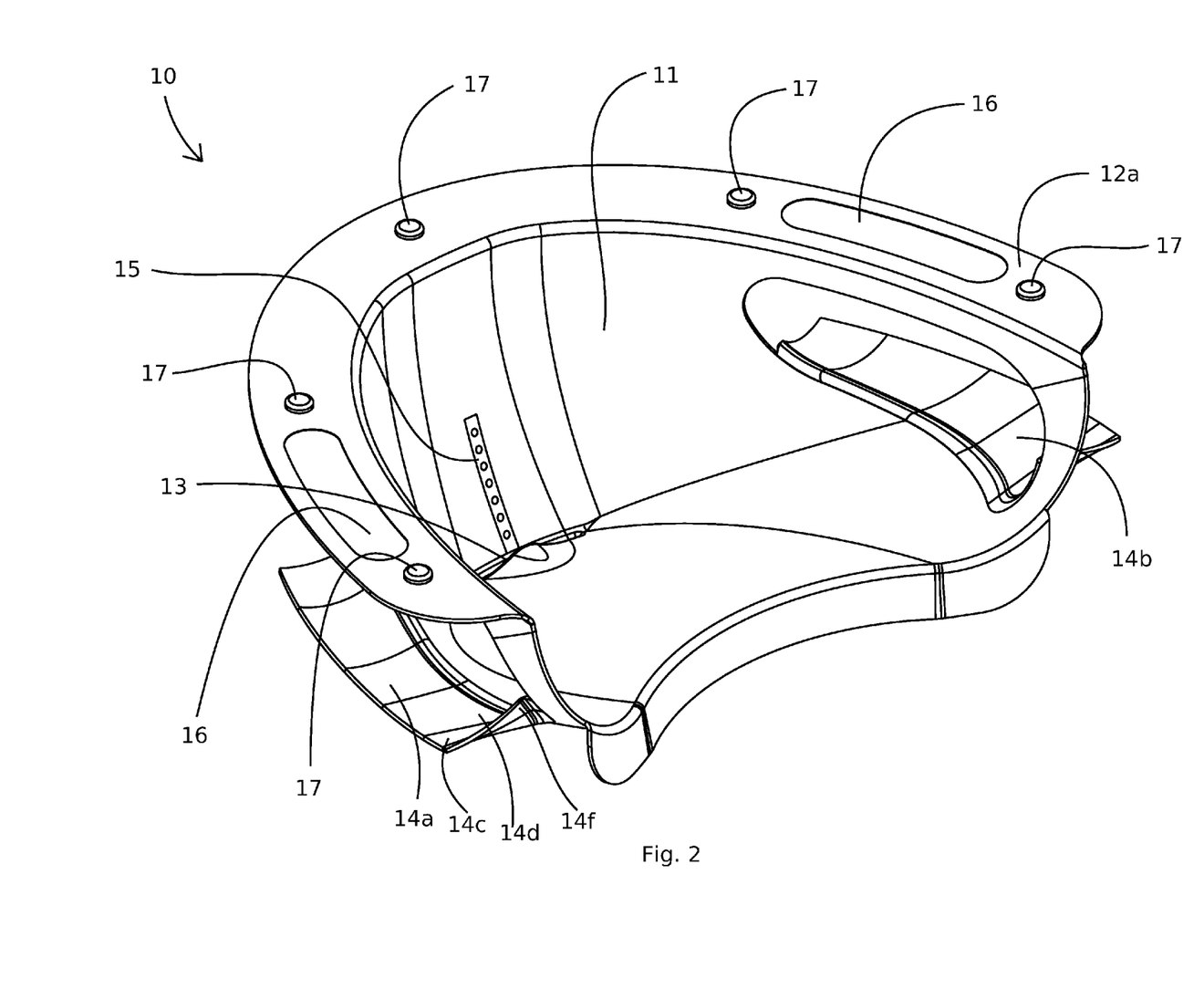
FIG. 2 is a perspective view of one embodiment of a urine specimen capture bowl.
Figure 3:
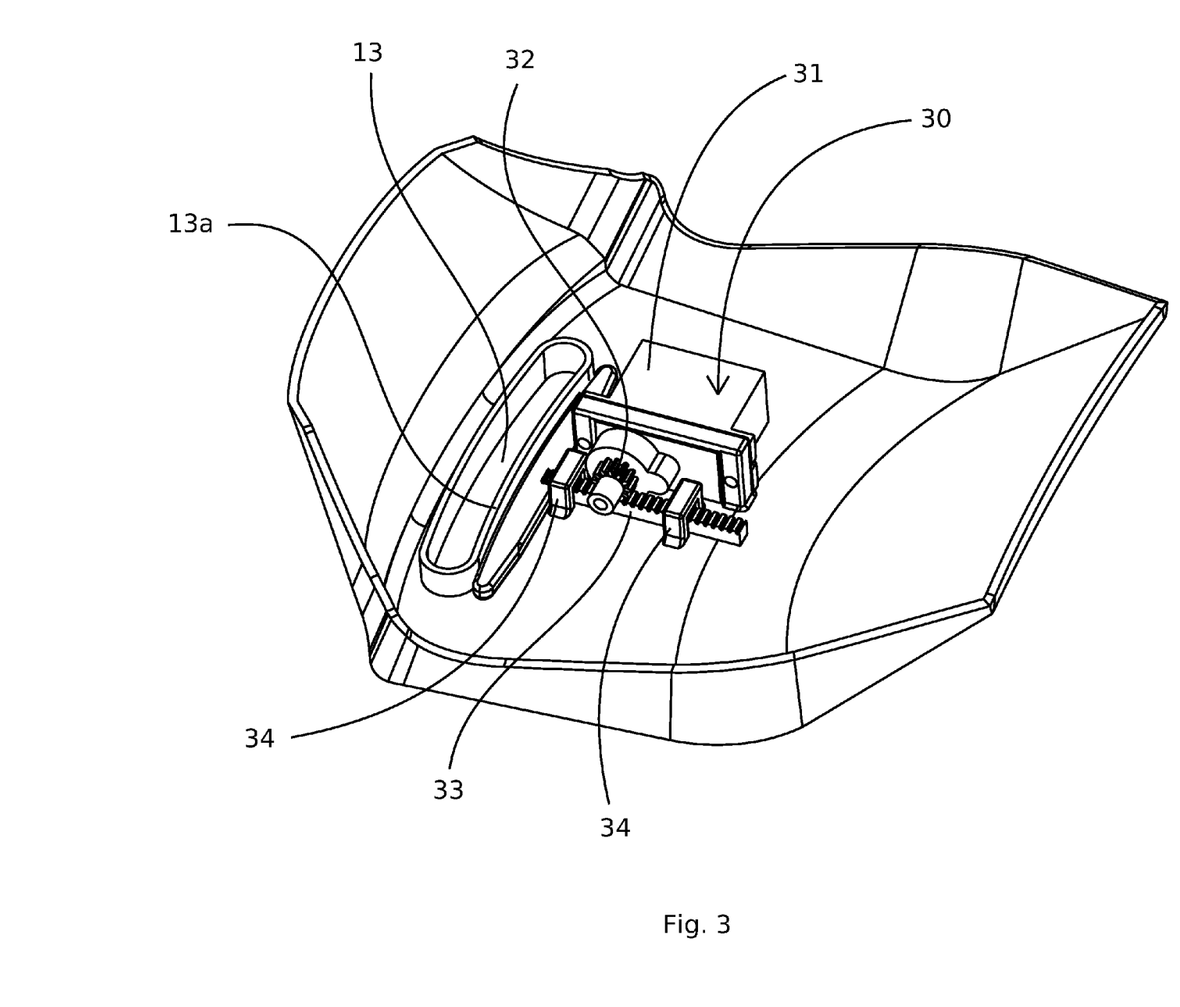
FIG. 3 is a perspective view of one embodiment of a urine specimen capture bowl closing mechanism.
Figure 4:
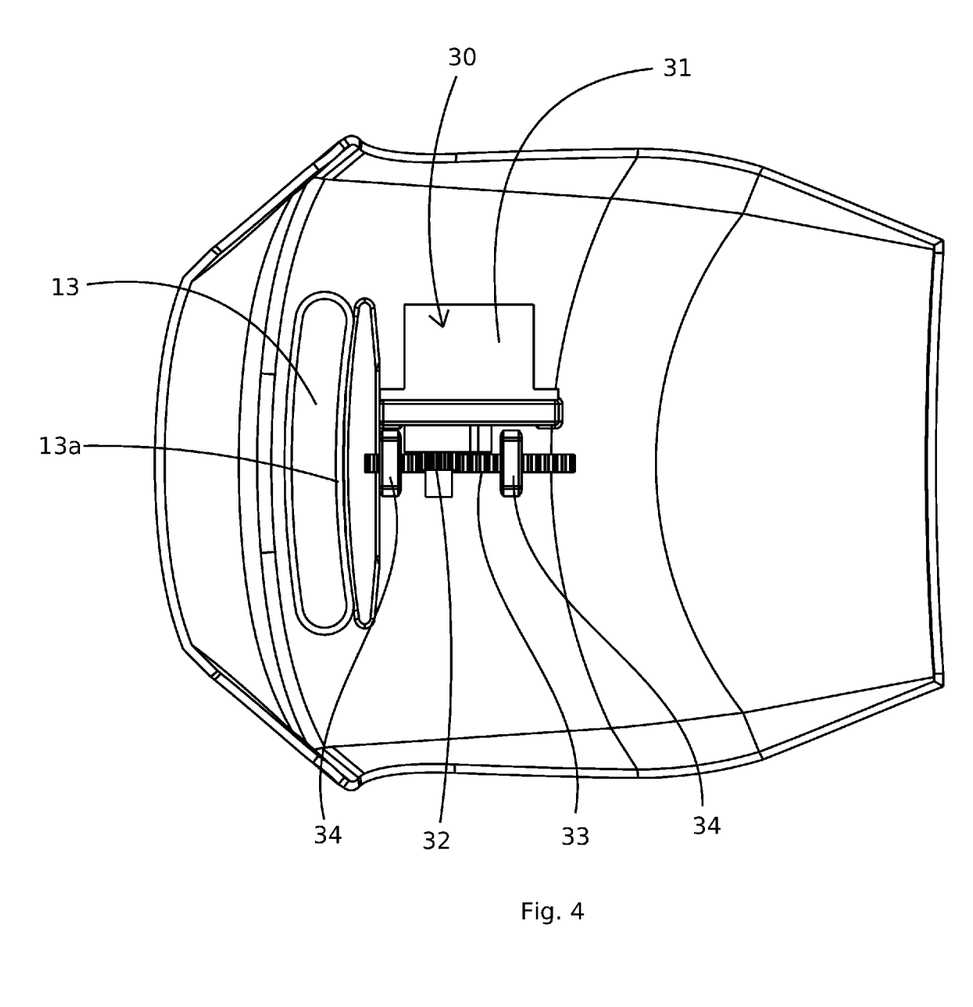
FIG. 4 is a top view of the urine specimen capture bowl closing mechanism of FIG. 3.

FIG. 2 shows a urine capture device that is configured to be inserted within the toilet bowl of an existing toilet. The urine capture device 10 comprises a capture bowl 11 that is supported by and connected to a mounting flange 12a that rests on top of the rim 22 of a toilet bowl. The urine capture bowl may be secured within the toilet bowl by such means as suction cups 17. Other means may also be used, for example, tape, silicone tabs that reversibly stick to the toilet bowl rim, hook and loop fixtures, etc. The urine capture device further comprises one or more flush water capture flange 14a and 14b. As shown in FIG. 2, two capture flanges 14a and 14b are shown extending from the sides of the urine capture bowl. Alternatively, or in addition to the side-extending capture flanges, one or more capture flange may also extend from the front portion of the urine capture bowl. The capture flanges are fluidly connected to and extend from the capture bowl in such a manner as to divert flush water into the capture bowl. For example, when the urine capture bowl is placed within a toilet bowl, the flush water capture flanges 14a and 14b are configured to extend outwardly a sufficient distance to be positioned under the rim holes 24 inside the toilet bowl from which flush water is expelled, thereby capturing flush water that is expelled from the rim holes into the toilet bowl during flushing of the toilet and directing the flush water into the urine capture bowl. Alternatively, the capture flanges 14a and 14b may be configured to extend outwardly a sufficient distance to touch the side of the toilet bowl, thereby capturing flush water passing down the side of a toilet bowl rim, and directing such flush water to the capture bowl. The flush water captured from the rim holes 24 of the toilet bowl is then used to rinse the contents of the capture bowl through an opening 13. Accordingly, each flush cycle removes the urine sample from the capture bowl and rinses the capture bowl with clean water, readying the capture bowl for a new urine specimen from a subsequent user. With this device, the need for visually inspecting and manually removing the urine content of the capture bowl is eliminated.

Also shown in FIG. 2 are pressure sensors 16 which can be used to detect the load of a user sitting down on the toilet and prepare the urine capture device for receiving a urine sample.

In some embodiments, discussed in more detail below, a urine specimen captured in the capture bowl is first analyzed before it is removed from and rinsed out of the capture bowl. It is understood that the functionality of the toilet flush water capture flange 14 will ordinarily be used in conjunction with a mechanism for retaining the urine sample in the capture bowl for a sufficient time for the specimen to be analyzed (i.e., determining of volume, analyzing urine content, etc.). Accordingly, another aspect of the invention relates to such a mechanism, which is discussed in more detail below.

The flush water capture flange represents a novel improvement on the prior art urine hat devices. As shown in FIG. 1, the capture flange is configured to extend outwardly from the capture bowl a sufficient distance and at a suitable angle that it is capable of capturing flush water that is discharged from the flush water rim holes 24 (shown in FIG. 4) that are typically located underneath the toilet bowl rim of an ordinary toilet. A flush water capture flange may be configured, for example, to fit the specific dimensions of a particular brand and model of a toilet. In such cases, the position, number, length of extension and angle of extension can be tailored to the specific dimensions of that toilet bowl.

In one particular embodiment, the capture flange 14 is sloped downwardly from the outer edge 14c of the capture flange to the inner edge 14d of the capture flange and into the capture bowl 11, so as to allow water captured by the flange 14a from the toilet bowl rim holes 24 to flow into the capture bowl under the force of gravity. In some embodiments, the capture flange may also be configured with features that direct the flow of captured flush water. For example, in some embodiments, the capture flanges may include fluid flow trenches to direct the flow in a particular direction. In other embodiments, the capture flanges may include raised sides 14f to keep the flow of flush water directed downwardly into the capture bowl.

In other embodiments, the present invention further contemplates a urine specimen capture device design that is capable of fitting toilet bowls of various shapes and sizes. For example, in one embodiment, the present invention contemplates the use of a capture flange that is flexible. A flexible capture flange may be constructed of any suitable material that is water impervious and can flex to accommodate toilet bowls of various shapes and sizes. For example, a flexible capture flange may be construed of rubber, silicone, soft plastic, PVC (polyvinyl chloride) or other material generally known to those skilled in the art. Alternatively, flexible capture flanges may also be constructed in the form of a hinged flange, or a telescoping flange, so as to allow the capture flange to bend at different angles or extend to varying lengths to accommodate variable widths and distances of smaller or larger toilet bowls.

In some embodiments, the capture flanges need only be sufficiently long that they capture flush water discharged from a rim hole beneath the rim of a toilet bowl. For example, it is sufficient that the capture flange extend under one or more rim hole, without actually abutting or engaging with the inner surface of the toilet bowl, provided the flush water discharged from the rim hole is captured by the outer edge of the capture flange.

In another embodiment, the capture flange extends from the capture bowl a distance sufficient that the outer edge of the capture flange, when inserted within the toilet bowl, abuts the inside surface of the toilet bowl. This particular arrangement provides the functionality of capturing flush water that is not only discharged from a rim hole, but also capturing flush water that may flow down the side of the inside surface of the toilet bowl (for example, where the rim holes may be positioned so closely to the inside surface of the toilet bowl, or positioned on the upper inside surface of the toilet bowl itself, such that the water discharged cannot be captured by simply placing the flange underneath the rim hole). The use of a flexible material for the capture flange, as described above, may be advantageously used in this embodiment to cause the capture flange to abut against the inside surface of the toilet bowl and create a sufficiently tight fit against the toilet bowl that the flexible flange captures a sufficient amount of the water flowing out of the rim holes and into the toilet bowl to properly flush and clean the urine capture bowl.

In yet another embodiment, the capture flange may have an outer edge that is curved to substantially conform to the curvature of the inside surface of the toilet bowl. This embodiment further assists in assuring that sufficient amount of the flush water flowing out of the rim holes is captured and diverted to the capture bowl.

In yet another embodiment, the toilet urine specimen capture device of the present invention may include a plurality of capture flanges, positioned at or extending from different locations on the capture bowl. In some embodiments, the urine specimen capture device may have two capture flanges positioned on each side of the capture device, as illustrated by capture flanges 14a and 14b in FIG. 2. Additional capture flanges may be added in other locations, for example, a capture flange may extend from both sides, and/or from the front of the capture device. Alternatively, as in the embodiment shown in FIG. 5, a single capture flange 14 may be positioned at the front of the capture bowl.

In yet another embodiment, as shown in FIGS. 1 and 2, the mounting frame 12 of the urine specimen capture device is connected to the capture bowl 23 and supports the capture bowl within the toilet bowl 12. In some embodiments, the capture bowl is supported on the toilet bowl rim 22. For example, the mounting frame 12 may include a rim mounting flange 12a, as shown in FIGS. 1 and 2, which rests on top of the toilet bowl rim 22, thereby supporting the capture bowl inside the toilet bowl. The rim mounting flange 12a may, for example, comprise a continuous flange that extends across the front portion of the toilet bowl rim. In another embodiment, the rim mounting flange may comprise two or more segments that rest on the toilet bowl rim. In yet other embodiments, the mounting frame may mount to the inside surface of the toilet bowl rim by frictional force, or by extending the mounting frame a sufficient distance within the inside of the toilet bowl rim such that it is retained in place within the circular confines of the toilet bowl (i.e., extending more than half way around, so that it forms more than a half circle). In yet another embodiment, the mounting frame could also be mounted under the toilet bowl rim, for example, by extending the frame within the inside of the toilet bowl that it is retained in place. It is understood that various mounting configurations are possible, without departing from the scope and intent of the present invention.

In another aspect, as shown in FIG. 2-6, the present invention further provides a urine specimen capture device having a capture bowl with an opening 13 at the bottom of the capture bowl 11. The opening 13 at the bottom of the capture bowl 11 allows the contents of the capture bowl to flow out of the capture bowl when analysis of a urine specimen is completed, and further allows the flush water captured by the capture flanges to rinse the capture bowl clean of any residual urine remaining in the capture bowl, thereby preparing the capture bowl to receive a urine specimen from a subsequent user.

In some embodiments, the opening 13 at the bottom of the capture bowl 11 may further include a valve 13a that selectively closes or opens the opening as needed to either retain a urine specimen in the capture bowl or to release the specimen from the capture bowl and allow flush water to rinse the contents of the capture bowl and be discharged out of the capture bowl through the opening. For example, FIGS. 2-6 illustrate an opening 13 at the bottom of the capture bowl, in conjunction with a pinch valve comprising a flexible sleeve 13a that can be opened or closed by a rack and pinion gear 30. The rack and pinion gear, as illustrated generally in FIGS. 3-6, is comprised of a motor 31, which turns a circular wheel 32, which in turn actuates a linear pinching arm 33 to move forward and pinch the flexible sleeve 13a closed. A rack and pinion is a type of linear actuator that comprises a pair of gears which convert rotational motion into linear motion. A circular gear called "the pinion" is connected to a motor, and when the rotational movement of the motor causes the pinion to rotate, the pinion engages teeth on a linear "gear" bar called a "rack". The rotational motion applied to the pinion causes the rack to move forward, thereby translating the rotational motion of the pinion into the linear motion of the rack. The reverse rotational motion is then applied to the pinion to cause the rack to move backward, thereby removing pressure from the flexible pinch valve and opening the hole in the bottom of the bowl. Other suitable mechanical means are, of course, known to those skilled in the art, which could be substituted for a rack and pinion gear to move the pinching arm 32 forward to pinch the flexible sleeve closed or backward to "unpinch" the flexible sleeve and open the flexible sleeve. For example, a screw gear or worm drive could also be used. For example, one suitable type of screw gear is a motorized rotating threaded shaft (screw) which pushes a projection from a shaped nut (which projection comprises or is connected to a pinching arm) forward and backward against a soft flexible valve, sealing it against the passage of fluid from the capture bowl. The present invention further contemplates other possible valves that open and close the aperture that defines the opening. For example, a solenoid valve, a pneumatic valve, or a hydraulic valve would also be suitable types of actuating mechanisms for opening and closing various types of valves (i.e., gate valves, ball valves, check valves, butterfly valves, etc.) for use in the present invention. Thus, it is understood that any type of valve capable of opening and closing the opening of the capture bowl may be used in the present invention.

In yet another aspect, the present invention provides a valve actuator that actuates the capture bowl valve and/or the flushing of the toilet. The valve actuator is configured to selectively close the valve to prevent fluid from flowing through the opening, and selectively open the valve to allow fluid to flow through the opening. The valve actuator may be any type of device that initiates an electric current to actuate the valve. For example, in some embodiments, the valve actuator is a valve switch, which may be a simple manual on/off switch or a button that the user or operator presses to alternately open and close the valve. Alternatively, the valve switch may comprise a door opening sensor that detects the opening of the bathroom door, or that detects the opening of a toilet seat lid. In other embodiments, the valve switch may comprise a more technically advanced mechanism connected to a mobile or wireless device. For example, the valve actuator may comprise a wireless keypad or touch screen that activates the valve upon entry of a code on a directly wired or wireless keypad or touch screen. As shown in FIG. 1, one type of valve actuator may be a user proximity sensor 26, which detects the present of the user, or the departure of the user from the toilet housing the urine capture device.

It is understood that any of various types of sensors may be used to detect the presence of a user on a toilet. Various types of sensors are known to those skilled in the art, any one of which may be used to detect the presence of a user on a toilet. For example, such a sensor may be a pressure sensor, such as pressure sensor 16 (shown in FIG. 1) that detects pressure on a toilet seat from a user sitting on the toilet seat, for example, using a strain gauge, a load sensor, a basic contact detector, a capacitative sensor that detects a current flow through the bare leg of a user, or a momentary push button switch. Alternatively, the sensor may comprise a proximity sensor 26 that detects the presence of a user near the proximity sensor, for example, an optical proximity sensor, such as an infrared proximity sensor, an ultrasonic range detector, or a "magic eye" type beam-interrupt detector, or reflective proximity detector. Thus, it is contemplated that the sensor may comprise any type of sensor known to those skilled in the art that is capable of detecting the presence of a user on a toilet above the capture bowl.

In yet another aspect, the present invention further provides a fluid level sensor 15 integrated into the side of the capture bowl 11 (as shown in FIG. 2). Various types of fluid level sensors are known and used in the art, and may be used to advantage in accordance with the principles of the present invention. As described above, one of the objectives of a urine hat is to determine, and sometimes to monitor over time, the urine output of a patient. The use of a urine hat that is capable of automatically measuring the urine output of a patient has significant advantages, including accuracy, higher user compliance rates, higher frequency of data points over time as a result of higher user compliance rates, etc. Typical fluid level sensors that may be used to advantage in the capture device of the present invention include, for example, a capacitance transmitter, which measures the change in capacitance between two plates produced by changes in level of a liquid. A capacitative fluid level sensor can be mounted to the outside of the capture bowl and measure through the wall of the (non-metallic) container, and can be optimized to ensure precise fluid-level measurements with a high level of accuracy. The design can use a traditional printed circuit board for a flat surface, or a thin, flexible circuit board to accommodate a curved surface of the capture bowl. Capacitative fluid level sensors are available, for example, from such companies as Molex, Lisle, Ill., USA. Another suitable fluid level sensor may include, for example, a solid-state sensor having a resistive output that varies with the level of a fluid. Such a sensor's envelope is compressed by the hydrostatic pressure of a fluid in which it is immersed, which results in a change in resistance that corresponds to the distance from the top of the sensor to the surface of the fluid. Thus, the sensor's resistive output is inversely proportional to the height of the liquid: the lower the liquid level, the high the output resistance; the higher the liquid level, the lower the output resistance. Such continuous fluid level sensors are available commercially, for example, under the brand name eTape™ (Milone Technologies, Sewell, N.J., USA). Any suitable fluid level sensor can be used in the urine specimen capture device in accordance with the principles described herein.

In yet another aspect the present invention provides a toilet flush mechanism that is configured to actuate the analytic and mechanical components of the disclosed device. In some embodiments, the capture device comprises a toilet flush mechanism that is configured to actuate the flush valve. For example, the flush valve in the opening of the capture bowl may be set to a default closed position so that a user may sit on the toilet seat and deposit a urine sample in the capture bowl without draining (or only partially draining) through the opening, such that the urine sample is partially or entirely collected in the capture bowl. With the urine sample now collected in the capture bowl, the analytic device may analyze the components of the urine specimen. Upon actuation of the toilet flush mechanism, a signal may then be sent to the flush valve to open and drain the contents of the capture bowl. Thus, the flush valve may be operably connected to and configured to open upon actuation of a toilet flush mechanism.

Figure 5:
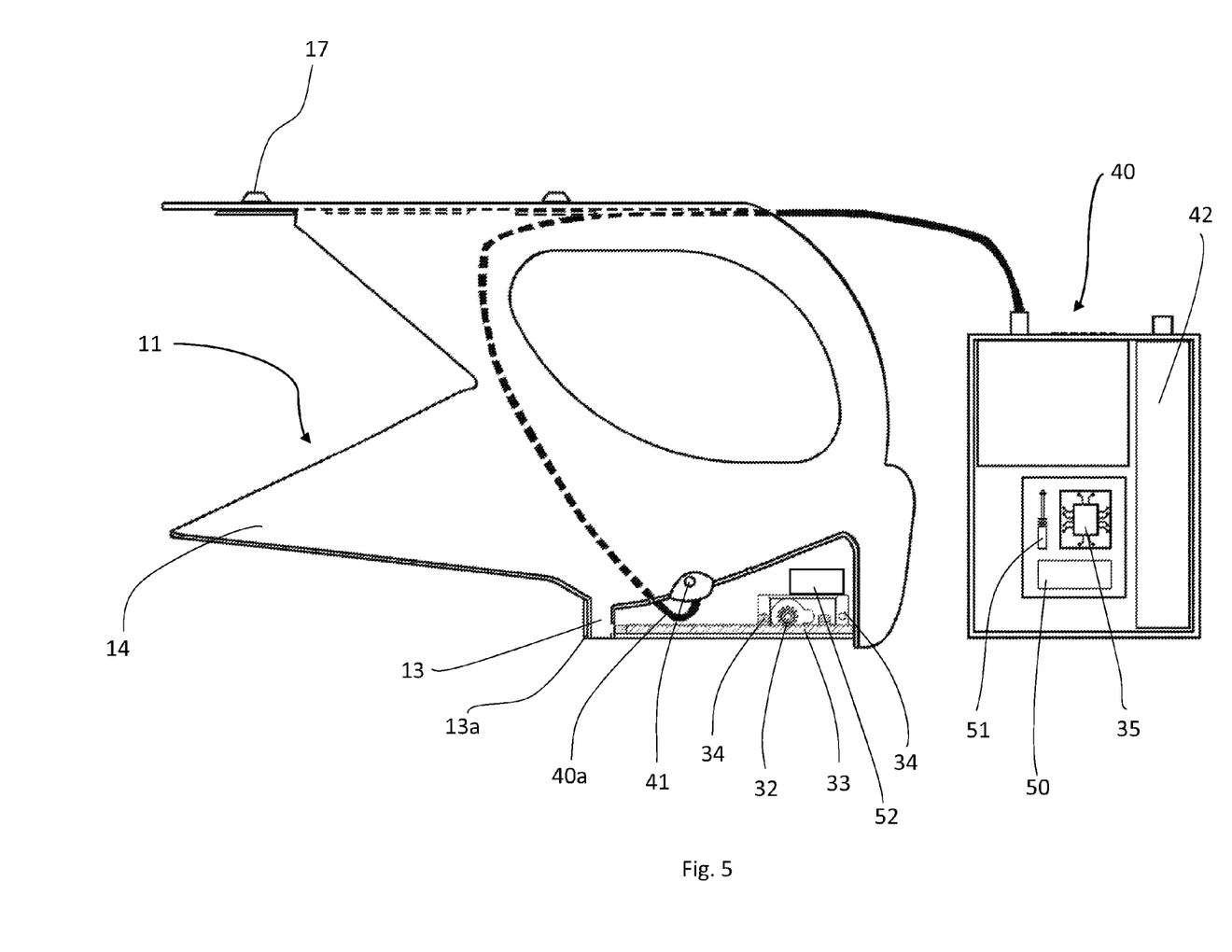
FIG. 5 is a side view of a urine specimen capture bowl, further showing the electronic control features.
Figure 6:
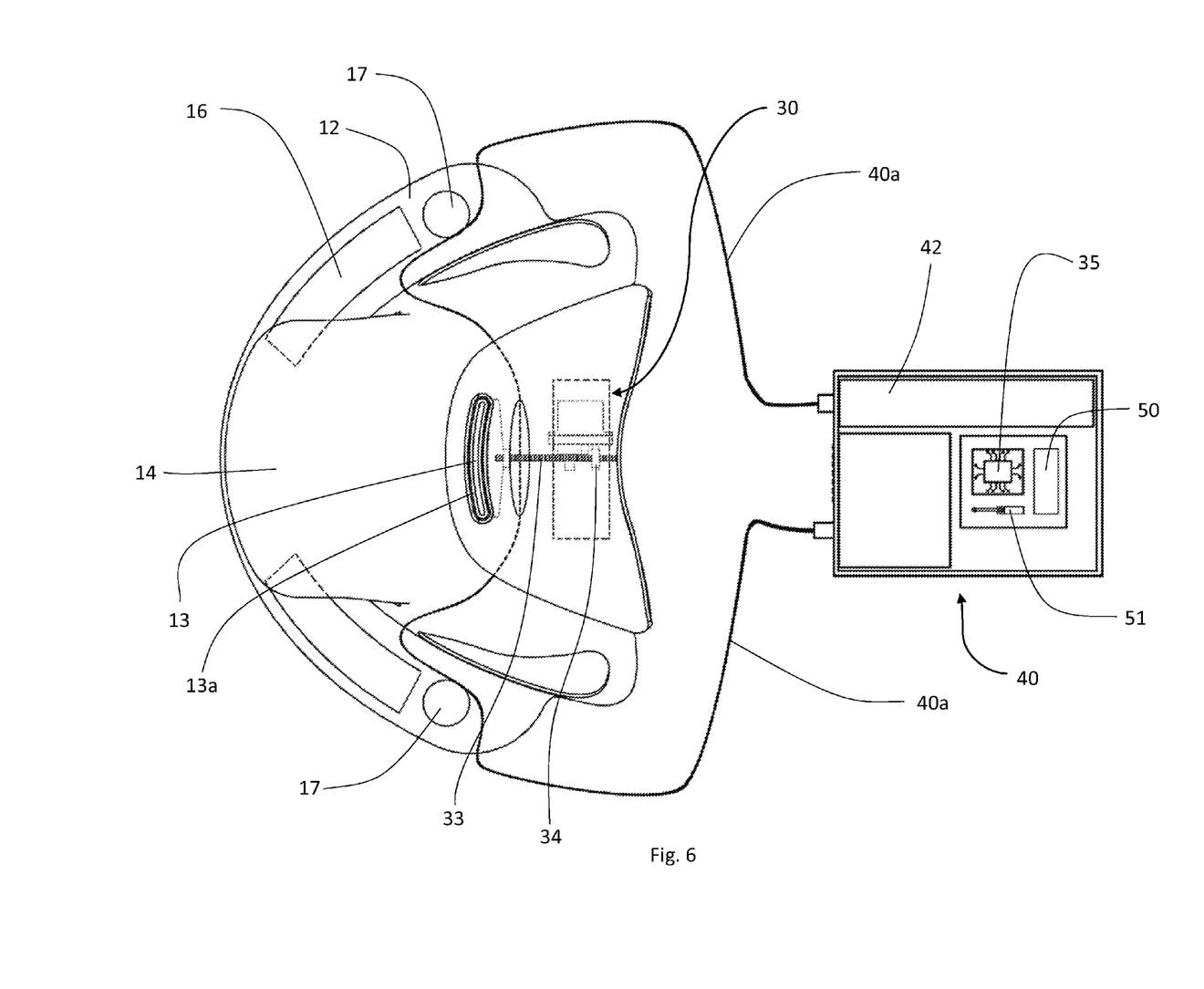
FIG. 6 is a top view of an embodiment of a urine specimen capture bowl.

In yet another aspect the present invention provides a suitable analytic device capable of detecting and/or measuring analytes in a urine sample. In some embodiments, as shown in FIGS. 5 and 6, the analytic device may comprise a spectrometer 40 that is connected to a urine capture device 41 via fiber optic cables 40a. A light source 42 is provided to generate light, which is used to measure properties of the analytes in the urine specimen. Also shown in FIG. 5 is a microprocessor 35 and control board 50 which together control the operation of the system including, but not limited to, operating the spectrometry device; processing the data received from the spectrometry device; connecting to the Cloud/Central Server/(however we reference our cloud) and uploading the data received from the spectrometry device; providing feedback from sensors installed on the device; providing communication to a user controlled input device; maintaining registered user data; controlling any necessary function of the device including, but not limited to, motor/valve function, user feedback indicators, power system operation. A wireless transmitter 51 is also shown, which may also be used to communicate through various wireless communication protocols including, but not limited to, WiFi, Bluetooth, cellular service provider and may be used in conjunction with, instead of or replaced by a user interface device including, but not limited to, a keypad, scanner, cell phone or tablet. Battery 52 supplies power to the system.

Figure 8:
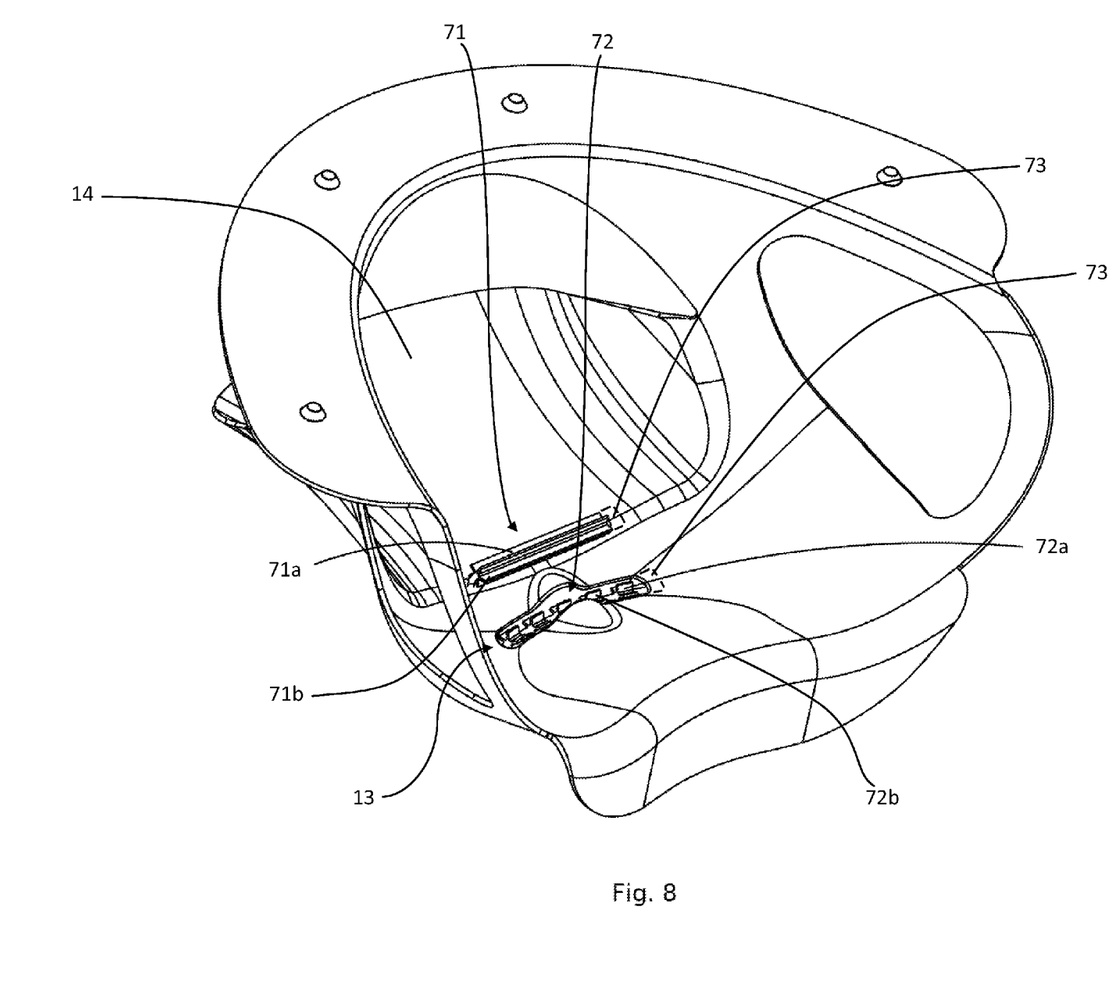
FIG. 8 shows a paddle-type power generator for generating power from flush water.

In some embodiments of the present invention, the analytic device of the present invention may comprise a generator that powers the analytic device. In a particular embodiment, the power generating system is integrated with the flush mechanism, and the generator generates power from flushing water. For example, in one particular embodiment, a paddle type power generator converts water flow into electrical energy. FIG. 8 shows two possible embodiments of power generators 71 and 72 that may be used individually or together. Power generator 71 is shown positioned at the bottom of a flush water capture flange 14. The power generator 71 comprises a plurality of paddles 71a, 71b, etc., comprised of a plurality of continuous paddles, which are impelled by flush water and cause the paddle system to rotate. The rotational energy of the paddles can then be converted to electrical energy by any type of electrical power generator 73 known to those skilled in the art. Similarly, another power generator 72 is shown positioned above (or below) the valve 13. The power generator 72 comprises a plurality of paddles 72a, 72b, etc., comprised of a plurality of discontinuous paddles (each paddle comprising a plurality of small extensions that are spaced apart), which are impelled by flush water passing through the valve and cause the paddle system to rotate. The rotational energy of the paddles can then be converted to electrical energy by any type of electrical power generator 73 known to those skilled in the art. The electrical energy generated from the paddle generators can then be stored in a power storage device, or used directly, to power the electrical components described herein.

The present invention contemplates that any suitable type of spectrometer technology or equipment may be utilized that is capable of analyzing components of urine, including organic compounds, as well as inorganic compounds. For example, spectroscopy may be used to detect the presence and quantity of such analytes as blood urea nitrogen (BUN), glucose, creatinine, protein, urea, ketones, oxalate, and albumin. Particular analytes of interest may include metabolites, such as estrone-3-glucuronide ($E_1G$) a major estrogen metabolite.

Suitable spectrometer technology platforms may include any type of spectroscopy that is suitable for analysis of organic and inorganic compounds typically found in urine. Such spectroscopy platforms may include, for example, any type of spectroscopy that relies upon electromagnetic radiation as a source of energy for observing the response of chemical compounds to such radiated energy. The interaction between the energy and the material may include, for example, adsorption of energy from the radiative source by the material, emission of radiative energy released by the material, elastic scattering and reflection by the material, impedance of transmittance of energy by the medium, inelastic scattering involving an exchange of energy between the radiation and the matter than shifts the wavelength of the scattered radiation (including Raman and Compton scattering), and coherent or resonance spectroscopy where the radiative energy couples two quantum states of the material in a coherent interaction that is sustained by the radiating field (including nuclear magnetic resonance, or NMR, spectroscopy). The particular type of spectroscopic platform may be selected by one of ordinary skill in the art, depending on the particular analyte of interest.

In one particular embodiment, such an analytic device may comprise a near-infrared (NIR) spectrometer. An NIR spectrometer capitalizes on the unique light-absorbing characteristics of individual molecules, referred to as "bands" and "overtones," to generate a "picture" of how the sample responds to different wavelengths of light. Typically, NIR spectroscopy will utilize wavelengths in the range of 700-3000 nm. Each wavelength of light, when passing through the sample, interacts differently based on the chemicals and analytes in the sample. Some wavelengths will be absorbed and some will be completely transmitted. By comparing the light that comes through the sample to a background reading taken with no sample in the collection area (or through a second fiber-optic light path), it is possible to see how the sample interacts with the light. Statistical analysis of this "picture," or light transparent image, is then used to assess the various levels of absorbance and identify the chemical makeup of the sample. Since measuring how a substance responds to infrared light is a straightforward, safe and non-destructive process, and can be used for a variety of monitoring procedures. NIR spectroscopy may be used, for example, to detect the presence and quantity of such analytes as blood urea nitrogen (BUN), glucose, creatinine, protein, urea, ketones, oxalate, and albumin.

In one particular embodiment, the use of a Fourier Transform Infrared spectrometer (FT-IR) is contemplated. FT-IR spectrometers comprise a two-beam optical interferometer, referred to as a Michelson interferometer. A beam splitter splits the incident beam into two paths: one of the beams is reflected by a moving mirror, and the other is used as a reference when reflected by a fixed mirror. The moving mirror controls the optical path, or simply the delay, of the first beam and thus the two reflected beams interfere producing a pattern that corresponds to the spectral content of the input light. The latter is captured by the single photo detector generating an "interferogram". The spectrum of the input light is directed generated by applying a Fourier Transform over the interferogram. Suitable FT-IR spectroscopy instruments are commercially available, for example, from NeoSpectra (formerly Si-Ware, Flintridge, Calif.).

Other suitable spectroscopy technologies include digital light processing (DLP) grating technology. A DLP spectrometer works by using a diffraction grating to split the incoming light into different wavelengths and then uses a DLP chip to more an array of mirrors individually and reflect only certain wavelengths of light at a time to the photo detector or ingaas detector that measures the intensity of light. Suitable DLP spectrometers are commercially available, for example, from such companies as Texas Instruments. Other suitable spectroscopy technologies include variable fabry-perot interference filters (FPI), non-dispersive, and dispersive.

Furthermore, in addition to determining the concentrations of specific analytes, NIR spectra also have the potential to serve as surrogate indicators for blood components and other physiologic markers not typically measured in urine. Given these observations, an NIR spectrometer embedded in a urine hat can be a powerful way to obtain accurate health-related information from human urine.

Accordingly, in another aspect, the present invention provides a urine capture device comprising a capture bowl, a spectrometer configured to analyze the contents of the capture bowl and a mounting frame connected to the capture bowl, wherein the mounting frame is configured to support the capture bowl within a toilet bowl on a toilet bowl rim. As shown in FIG. 1, a spectrometer 40 is provided in connection with the capture bowl. The spectrometer 40 may comprise, for example, a NIR spectrometer. In some embodiments, the spectrometer is isolated from the urine deposited in the capture device by a light transparent window 41 in a wall of the capture bowl 11. Alternatively, the spectrometer may be combined with a fiber optic cable that is placed directly into the capture bowl, without a light transparent window, such that the fiber optic cable is used to transmit analyte information to the spectrometer.

In another embodiment, the spectrometer may also be operably connected to the operation of the capture device, such that the spectrometer initiates a reading or analysis of the contents of the capture bowl when the urine level reaches a predetermined level such that there is sufficient urine present to reach the level of the light transparent window 41 and enable the spectrometer to take a reading. Thus, in some embodiments, the fluid level sensor is operably connected to the spectrometer, wherein the spectrometer is actuated upon the fluid level reaching a designated level.

Operation and Use

In operation, the basic concept of the integrated urine hat spectrometer is that when a user sits down on the toilet, a pressure sensor 16 is activated, which signals the motor 31 to turn and rotation of gear 32. Rotation of gear 32 causes shaft 33 to move forward and push against soft rubber valve 143a, sealing it against the passage of urine. The user can then deposit urine into the capture bowl 11. When the urine level reaches the lowermost level of the liquid sensor 15, sufficient to obtain a measurement, a signal is transmitted to the microprocessor 35, which activates a spectrometer 40. Light from the spectrometer passes through the fiber optic cables 40a and light transparent window 41, interacts with the sample and returns to spectrometer 40. The resulting data is transmitted to the microprocessor 35 and sent via a wireless transmitter 51 to the user's smart phone, mobile device or computer. The data can also be communicated to the cloud for analysis.

When the user has finished and stands up, the pressure sensor 16 is released. Motor 31 reverses direction, opening the valve formed by the flexible sleeve 14 around the opening 13 of the capture bowl and allowing the urine to drain. The user flushes the toilet and water from the flush is captured by the flush capture flanges 14, thereby cleaning and clearing the basin in preparation for the next use.

Urine Capture Slit

In another aspect, the present invention further contemplates a structure for capturing a urine sample for purposes of spectroscopic analysis. In one embodiment, the urine sample capture structure comprises a capture slit disposed on a surface exposed to urine, wherein the slit is configured to retain a sufficient portion of urine to obtain spectroscopic data on the urine sample. In one embodiment, one or more spectroscopic optical cable is operably connected to the capture slit, such that while a urine sample is retained within the capture slit the optical cable can collect and transmit spectroscopic data to a spectrometer and the contents of the urine sample can be detected and analyzed. Thus, during use of the urine capture slit, at least a portion of the urine is retained within the narrow slit, while spectroscopic data is obtained via the spectroscopic optical cables.

It is understood that the urine capture slit feature described herein may be disposed on any suitable structure on which urine may be or typically is disposed. For example, the urine capture slit may be disposed on a typical toilet bowl, a urinal or a urine hat.

The urine capture slit may be disposed within and flush with the surface of a toilet bowl, urinal or urine hat. Alternatively, the urine capture slit may be integrated into a raised mound 62a and 62b that is raised above (i.e., not flush with) the surface of the toilet bowl, urinal or urine hat. As described in more detail below, the raised mound functions to divert the urine specimen and flush water toward the urine capture slit.

In some embodiments, urine capture slit has a length, width and height that can accommodate an optical cable in the sides of the urine capture slit, and that is sufficient to draw into and retain a portion of the urine sample within the urine capture slit by capillary force, and also permit the urine capture slit to be easily and substantially completely flushed with water from a standard toilet flush. For example, in some embodiments, the length of the urine capture slit may range from about 2.5 mm (about 0.1 inches) to about 25 mm (about 1 inches), or from about 2.5 mm (about 0.1 inches) to about 9.5 mm (about 0.375 inches). In one particular embodiment, with length of the urine capture slit is about 6.35 mm (about 0.25 inches) long. The height of the urine capture slit may, in some embodiments, range from about 2.5 mm (about 0.1 inches) to about 31.75 mm (about 1.25 inches). In one particular embodiment, the height of the urine capture slit is about 6.35 mm (about 0.25 inches), which is sufficient to allow a spectroscopic optical cable and any necessary support structures to be integrated into the sides of the urine capture slit. In some embodiments, the urine capture slit has a width that is sufficient to draw into and retain a portion of the urine sample within the urine capture slit by capillary force. For example, suitable urine capture slit widths that will effectively draw into and retain a portion of the urine sample within the urine capture slit by capillary force will range from about 0.5 mm to about 2 mm. In some embodiments, the width of the urine capture slit will range from about 0.75 mm to about 1.5 mm. In other embodiments, the width of the urine capture slit will about about 1 mm.

In another aspect, the urine capture slit of the present invention has internal sides having a hydrophilic surface that will draw a portion of the urine sample within the urine capture slit by hydrophilic forces. In some embodiments, the urine capture slit will also be comprised of materials that are non-corrosive in an environment exposed to urine and/or feces (which may potentially enter into the urine capture slit). For example, suitable hydrophilic surfaces may comprise such materials as metal, ceramic, or plastic. Suitable metals include, for example, stainless steel. Suitable plastic material includes, for example, polyamides, polyacrylic amides, polyurethanes with polyethylene glycol ether soft segments, ethoxylated graft polymers, and styrene materials, etc. In one particular embodiment, the hydrophilic material is ABS (acrylonitrile butadiene styrene). In some embodiments, polymers having a non-hydrophilic structure may be chemically altered to have a hydrophilic surface by mixing them physically or reacting them chemically with hydrophilic products or components. For example, ethoxy or polyacrylamide groups may be used to increase the hydrophilic properties of a polymer.

In another embodiment, the urine capture slit of the present invention may further include a raised mound on the surface exposed to urine, wherein the urine capture slit is disposed within the raised mound. The raised mound is generally configured to direct urine toward and into the urine capture slit, thereby facilitating use of the spectroscopic analysis of the urine by the spectroscopic optical cables disposed within the urine capture slit. In some embodiments, the length, height and width of the raised mound may be approximately the same as or slightly larger than the length, height and width of the urine capture slit, as described above. For example, in some embodiments, the length of the raised mound may range from about 2.5 mm (about 0.1 inches) to about 25 mm (about 1 inches), or from about 2.5 mm (about 0.1 inches) to about 9.5 mm (about 0.375 inches). In one particular embodiment, with length of the raised mound is about 6.35 mm (about 0.25 inches) long. The height of the raised mound may, in some embodiments, range from about 2.5 mm (about 0.1 inches) to about 31.75 mm (about 1.25 inches). In one particular embodiment, the height of the raised mound is about 6.35 mm (about 0.25 inches) long, which is sufficient to allow a spectroscopic optical cable and any necessary support structures to be integrated into the sides of the urine capture slit. In some embodiments, the width of the raised mound is sufficient to slow the flow or urine and/or direct the urine toward the urine capture slit. For example, in some embodiments, the width of the raised mound may range from about 50 mm (about 2 inches) to about 125 mm (about 5 inches). In some embodiments, the width of the raised mound may range from about 75 mm (about 3 inches) to about 100 mm (about 4 inches). In other embodiments, the width of the raised mound is about 75 mm (about 3 inches).

The urine capture slit may be oriented in any direction suitable for capture of a urine sample. For example, in one aspect of the present invention, the urine capture slit is oriented in a direction substantially parallel to the flow of the urine, thereby maximizing the likelihood that a sufficient amount of urine is captured within the urine capture slit to enable spectroscopic analysis of the urine sample. In another aspect, the narrow slit is oriented in a direction substantially parallel to a flow of flush water, thereby maximizing the likelihood that a urine sample is rinsed from the urine capture slit following capture within the urine capture slit and spectroscopic analysis of the urine sample has been completed. The urine capture slit may, of course, be oriented at any intermediate angle relative to the flow of urine or the flow of flush water.

Figure 7A:
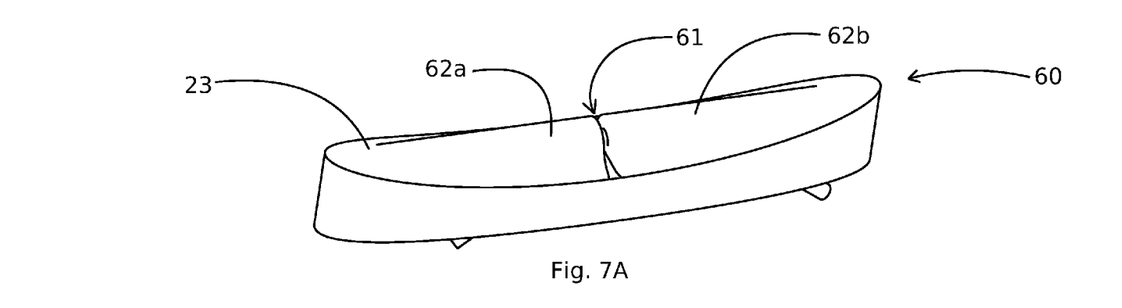
FIGS. 7A, 7B and 7C show various views of one embodiment of a urine capture slit.
Figure 7B:
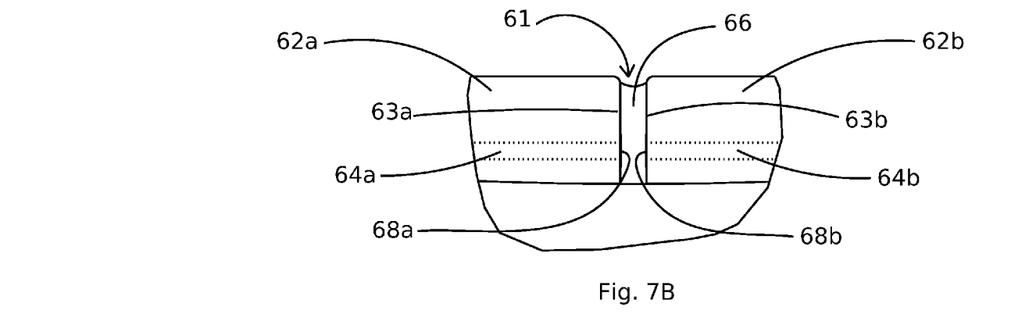
Figure 7C:
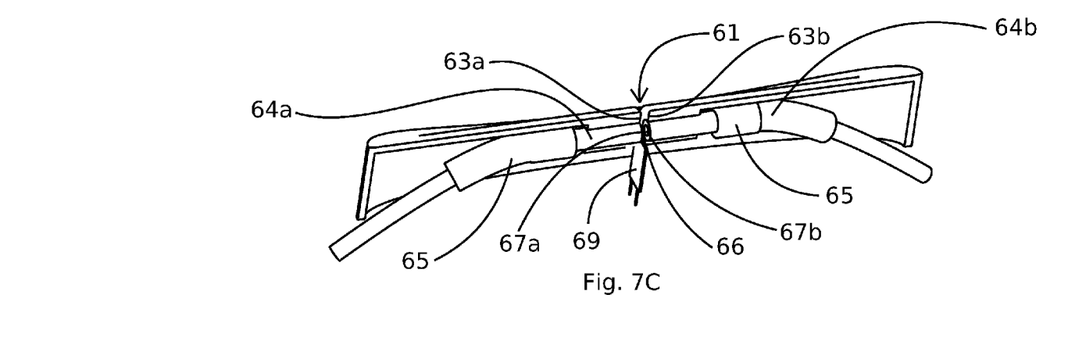

FIGS. 7A, 7B and 7C illustrate a particular embodiment of the urine capture slit described above. FIG. 7A is a perspective view of a urine capture device 60 having urine capture slit 61 disposed on the inside surface 23 of a toilet, urinal or urine hat. Also shown in FIG. 7A is a raised mound 62a and 62b on each side of the urine capture slit 61. The raised mounds 62a and 62b are configured to divert urine flow through the urine capture slit 61 (wherein it can be temporarily retained for analysis) and also to divert toilet flush water through the urine capture slit 61 where the toilet flush water can then rinse the urine sample from the urine capture slit.

FIG. 7B shows an expanded side view of the urine capture slit 61. The urine capture slit comprises internal sides 63a and 63b, comprised of a hydrophilic material that draws into and retains a portion of a urine sample 66 within the urine capture slit between the internal sides 63a and 63b. Internal side 63a and 63b will have an aperture 68a and 68b, respectively, through which the optical cables 64a and 64b can pass light from the spectrometer for spectroscopic analysis.

Alternatively, in some embodiments of the present invention, the width of the slit may be sufficiently wide that a urine specimen is not retained within the slit and the urine sample simply flows through the slit.

FIG. 7C shows a section view of the same urine capture slit 61 as shown in FIG. 7A, further showing the internal optical cables 64a and 64b used for spectroscopic analysis. The urine capture slit 61 comprises internal sides 63a and 63b, each of which have opposing apertures 68a and 68b, within which is disposed optical fibers 64a and 64b. Spectroscopic optical cables 64a and 64b are positioned on each of internal sides 63a and 63b, such that light from a spectrometer is able to pass from one end 67a of the optic cable 64a, through the captured urine sample, and into the other end 67b of the optic cable 64b, with an aperture 68a on one internal side opposing an aperture 68b on the other internal side. FIG. 7C further shows an embodiment having a temperature sensor 69 disposed adjacent to or within the urine capture slit 61 for the purpose of determining the temperature of urine passing through the urine capture slit. The optical fibers are operably optically connected to a spectrometer.

There is thus disclosed an improved urine specimen capture device. It will be appreciated that numerous changes may be made to the present invention without departing from the scope of the claims.

What is claimed is:

1. A urine specimen collection device, comprising:
   a capture bowl, the capture bowl comprising a surface exposed to urine;
   at least one capture flange, wherein the at least one capture flange extends from an outer rim of the capture bowl, and wherein an outer edge of the at least one capture flange fits substantially against a surface of a toilet bowl,
   a valve, wherein the valve is positioned within the capture bowl, and wherein the valve selectively opens and closes to release or retain urine in the capture bowl,
   a slit disposed on the capture bowl, wherein at least a portion of the urine is retained within the slit, and wherein the slit comprises a length approximately between 2.5 mm and 9.5 mm, a height approximately between 2.5 mm and 31.75 mm, and a width approximately between 0.5 mm and 2 mm.

2. The urine specimen collection device according to claim 1, wherein the capture bowl is disposed on a toilet bowl, urinal or urine hat.

3. The urine specimen collection device according to claim 1, wherein the surface exposed to urine comprises a raised mound, wherein the raised mound comprises a length approximately between 2.5 mm and 9.5 mm, a height approximately between 2.5 mm and 31.75 mm, and a width approximately between 0.5 mm and 2 mm, and wherein the slit is disposed within the raised mound.

4. The urine specimen collection device according to claim 1, wherein the length of the slit is oriented in a direction substantially parallel with a downward slope of the capture bowl.

5. The urine specimen collection device according to claim 1, wherein the length of the slit is oriented in a direction substantially parallel with a downward slope of a toilet bowl.

6. The urine specimen collection device according to claim 1, wherein the slit has internal sides having a hydrophilic surface.

7. The urine specimen collection device according to claim 1, wherein the slit comprises internal sides and wherein each internal side has an aperture opposing an aperture on the other internal side.

8. The urine specimen collection device according to claim 1, wherein the slit comprises internal sides and wherein the internal sides each have opposing apertures within which is an optical fiber.

9. The urine specimen collection device according to claim 8, wherein the optical fiber is optically connected to a spectrometer.

10. The urine specimen collection device of claim 1, wherein the slit comprises a length approximately between 2.5 mm and 25 mm and a width approximately between 0.5 mm and 1.5 mm.

11. The urine specimen collection device of claim 1, wherein slit comprises a length approximately 6.35 mm, a height approximately 6.35 mm and a width approximately 1 mm.

12. The urine specimen collection device of claim 3, wherein the raised mound comprises a length approximately between 2.5 mm and 25 mm and a width approximately between 0.5 mm and 1.5 mm.

13. The urine specimen collection device of claim 3, wherein the raised mound comprises a length approximately 6.35 mm, a height approximately 6.35 mm and a width approximately 1 mm.

* * * * *